United States Patent
Jiang

(10) Patent No.: US 10,456,437 B1
(45) Date of Patent: Oct. 29, 2019

(54) ANTIBACTERIAL WET WIPE FOR SKIN CARE

(71) Applicant: Shulan Jiang, Jiangmen (CN)

(72) Inventor: Shulan Jiang, Jiangmen (CN)

( * ) Notice: Subject to any disclaimer, the term of this patent is extended or adjusted under 35 U.S.C. 154(b) by 0 days.

(21) Appl. No.: 15/986,115

(22) Filed: May 22, 2018

(51) Int. Cl.
| | |
|---|---|
| *A61K 9/70* | (2006.01) |
| *A61K 36/61* | (2006.01) |
| *A61K 33/38* | (2006.01) |
| *A61K 36/752* | (2006.01) |
| *A61P 31/04* | (2006.01) |
| *A61K 47/10* | (2017.01) |
| *A61K 31/355* | (2006.01) |
| *A61K 47/32* | (2006.01) |
| *A61K 31/164* | (2006.01) |

(52) U.S. Cl.
CPC ............ *A61K 36/61* (2013.01); *A61K 31/164* (2013.01); *A61K 31/355* (2013.01); *A61K 33/38* (2013.01); *A61K 36/752* (2013.01); *A61K 47/10* (2013.01); *A61K 47/32* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 2012/0141571 A1* | 6/2012 | Lee | A01N 31/08 424/418 |
| 2013/0157957 A1* | 6/2013 | Pashkovski | A61K 8/42 514/18.8 |

FOREIGN PATENT DOCUMENTS

CN          103211727 A   *   7/2013

* cited by examiner

*Primary Examiner* — Susan T Tran
(74) *Attorney, Agent, or Firm* — Myers Bigel, P.A.

(57) ABSTRACT

The present invention provides an antibacterial wet wipe for skin care, which is prepared by adding an antibacterial skin care additive solution to a spunlaced non-woven fabric which is used as a base material, wherein the antibacterial skin care additive solution is prepared from the following components by mass fraction: Tea tree essential oil 5-10%, Nano silver 2-4%, Neroli essential oil 3-5%, Ceramide 1-1.5%, Glycerin 1-3%, Water-soluble vitamin E 0-3%, Emulsifier 0.1-0.5%, Deionized water balance. The preparation method of the antibacterial wet wipes for skin care is simple. And as adding the fungicides of tea tree essential oil and nano silver, and adding neroli essential oil, ceramide, glycerin, water-soluble vitamin E as moisturizing components, the antibacterial wet wipes for skin care of the invention not only have excellent antibacterial and disinfection effect, but also have whitening and moisturizing functions for skin care.

7 Claims, No Drawings

ANTIBACTERIAL WET WIPE FOR SKIN CARE

FIELD OF THE INVENTION

The invention relates to a wet wipe for skin care, especially relates to an antibacterial wet wipe for skin care.

BACKGROUND OF THE INVENTION

As people's growing emphasis on quality of life and health and safety, the use of sanitary wet wipes is more and more popular, especially when traveling and in outdoor activities, they are becoming a necessary article. At present, there are various kinds of wet wipes on the market with various categories and functions, such as for antibacterial, moisturizing, and odor-eliminating. However, these wet wipes usually have various problems, such as only having a limited antibacterial effects with moderate disinfecting and antibacterial properties; or some ingredients added to the wet wipes having stimulatory effects, such as containing alcohol components, or no moisturizing effect, and after using these wipes, the skin will dry quickly and become tightly, especially when used in winter, ladies will feel very uncomfortable and need to apply moisturizing cream for further skin care.

Therefore, there is a need for a new antibacterial wet wipe for skin care that has strong antibacterial and disinfection properties, high safety, and other skin care functions (e.g., moisturizing, whitening and the like).

SUMMARY OF THE INVENTION

To solve the above problems, the present invention aims to provide an antibacterial skin care wipe, which not only has excellent antibacterial and disinfection properties with improved safety, but also has whitening and moisturizing functions for skin care.

To achieve the aims of the present invention, the adopted technical solution is:

An antibacterial wet wipe for skin care, which is prepared by adding an antibacterial skin care additive solution to a spunlaced non-woven fabric which is used as a base material, wherein the antibacterial skin care additive solution is prepared from the following components by mass fraction:

Tea tree essential oil 5-10/%,
Nano silver 2-4%,
Neroli essential oil 3-5%,
Ceramide 1-1.5%,
Glycerin 1-3%,
Water-soluble vitamin E 0-3%,
Emulsifier 0.1-0.5%,
Deionized water balance.

Wherein, the tea tree essential oil is medical tea tree essential oil. Preferably, the tea tree essential oil has a mass fraction of 6-8% in the antibacterial skin care additive solution.

Preferably, the emulsifier is a hydrophilic emulsifier. And further, the emulsifier is a carbomer.

Preferably, the nano silver is derived from a nano silver solution with a mass percentage concentration from 500 ppm to 1000 ppm, the average particle size of the nano silver is 1-5 nm, and further if its particle size is smaller, the antibacterial activity is much higher.

Preferably, the spunlaced non-woven fabric is a wood pulp spunlaced non-woven fabric or a cotton spunlaced non-woven fabric. These two kinds of non-woven fabrics both are composed of natural fiber components, which have better water absorption property and softer feeling than common non-woven fabrics, thereby having no irritation to skin and are suitable for sensitive skin.

Tea tree essential oil is tea tree extracts, which mainly contains terpinen-4-ol, α-pinene, limonene, α-terpinene, γ-terpinene, α-terpineol. It not only has excellent antibacterial, antiviral, and anti-inflammatory effects, but also has many other functions such as astringing pores, calming your skin and so forth, which is a common material used in antibacterial wet wipes and skin care products for acne-removing and anti-inflammatory. Hammer K A et al. indicated in "Antifungal activity of tea tree oil" that, the tea tree oil can inhibit and kill saccharomycetes, dermatophytes and other filamentous fungi, and it also has a good inhibitory effect against *Candida albicans*; one study from the University of Western Australia suggested that the tea tree essential oil even has a certain inhibitory effects on *Staphylococcus aureus* (See "a randomized, controlled trial of tea tree topical preparations versus a standard topical regimen for the clearance of MRSA colonization"). Chinese patent CN 104224923 also demonstrated that the tea tree oil has good inhibitory effects on *Staphylococcus aureus, Escherichia coli*, and *Candida albicans* (with a bacteriostasis rate up to 100% in 2 min). And there are also many documents relating to the use of tea tree oil for treating skin inflammation and *acnes*. It can be seen that the tea tree oil is a good antibacterial agent, but its antibacterial and sterilization effects are still limited, as it can only work for some bacteria, fungi and viruses.

Nano-silver is a widely-recognized broad-spectrum bacteriostatic agent, which can kill more than 650 species of bacteria and can kill some normal bacteria, fungi, *mycoplasma, chlamydia* and the like at a low concentration of a few parts per million (see Table 1, in which lists the results of nano-silver solution sterilization test from the Chinese patent CN 201094754Y). And the bactericidal effects of nano-silver may not be affected by pH value, it is a broad-spectrum antibacterial agent without any drug resistant and is durable, safe and environmentally friendly ideal antibacterial material.

TABLE 1

Results of nano-silver sterilization test
(nano-silver concentration: 30 ppm)

| Species | Time (min) | | |
|---|---|---|---|
|  | 0 | 2 | 4 |
| *Staphylococcus aureus* | 17000 | 0.006 | 0 |
| *Pseudomonas aeruginosa* | 13000 | 0.005 | 0 |
| *Salmonella* | 13000 | 0.003 | 0 |
| *Candidemia* | 320 | 0.0005 | 0 |
| *Enterococci* | 410 | 0.00022 | 0 |

By combining the tea tree oil with nano silver for a synergistic effect, the antibacterial skin care additive solution added in the antibacterial wet wipes of the present invention has a broader spectrum of sterilization and disinfection, and longer lasting effects. In addition, the nano silver used in the invention has a particle size of 1-5 nm, which has higher antibacterial activity than other nano-silver with a larger particle size. And due to the unique properties of the tea tree oil, such as anti-inflammatory, calm and convergence for skin, the antibacterial wet wipes of the present invention added with the antibacterial skin care additive solution not only has an excellent antibacterial and sterilization activity but has the skincare benefits of tea tree oil.

The other two important components added to the antibacterial skin care wipes of the present invention are neroli essential oil and ceramide. Neroli essential oil can be extracted from plants of the Citrus. and the best neroli essential oil is extracted from the petals of bitter orange blossoms. The neroli essential oil has excellent whitening effect and good moisturizing, spots correcting effects, which can refresh the skin, promote skin circulation and improve elasticity of the skin. Ceramide is a main component of the epidermal stratum corneum, which can effectively prevent the moisture from being dispersed from the skin, and has an excellent moisturizing and skin repairing effect. The synergistic effects of neroli oil and ceramide may further enhance the skin's moisturizing effect, as well as whitening and repairing activities.

In addition, glycerin also has a good moisturizing effect, and can further enhance the moisturizing effect of the wet wipes.

Water-soluble vitamin E has some antioxidant properties and a certain moisturizing effect for the skin. It also has a certain cleaning effect.

The method for preparing the antibacterial skin care additive solution according to the present invention comprises: weighing the components according to the formula of the antibacterial skin care additive solution described hereinbefore, adding them into a stirred tank and stirring until the components are uniformly mixed. Then, the mixed solution is sterilized to obtain the antibacterial skin care additive solution of the invention.

In addition, except for using in wet wipes, the antibacterial skin care additive solution of the present invention can also be added to make-up remover cottons and the like.

Further, the sterilization method is radiation sterilization method, wet heat sterilization method or dry heat sterilization method, wherein the radiation sterilization method may be $Co^{60}$-$\gamma$ ray, ultraviolet or microwave sterilization method.

The present invention also provides a method for preparing the antibacterial wet wipe for skin care of the present invention, comprising sterilizing the spunlace nonwoven fabric, then flattening the spunlace nonwoven fabric in a container, adding sufficient amount of antibacterial skin care additive solution into the container and standing still for a certain period of time until the spunlaced nonwoven fabric is completely infiltrated. Wherein, the sterilizing treatment of the spunlaced non-woven fabric can be radiation sterilization method, wet heat sterilization method or dry heat sterilization method, wherein the radiation sterilization method may be $Co^{60}$-$\gamma$ ray, ultraviolet or microwave sterilization method.

The antibacterial wet wipe for skin care of the present invention not only has excellent antibacterial and disinfection effects but also has whitening and moisturizing functions for skin care. This is because the antibacterial skin care additive solution added to the antibacterial wet wipe of the present invention contains two fungicides of the tea tree oil and nano silver. The synergistic effects of the two substances enhances the sterilization and disinfection effects, extends the antibacterial period and broader the spectrum of the combined bacteriostatic solution. While the neroli essential oil and ceramide in the antibacterial skin care additive solution make the wet wipes of the present invention have good skin moisturizing effect, and also have certain whitening and repairing effects; glycerin is a commonly used skin care moisturizer which also has a good skin moisturizing effect, and the addition of water-soluble vitamin E makes the wet wipes have a certain degree of anti-oxidation effect, and further strengthens the moisturizing and cleaning effect. When the wet wipes added with the antibacterial skin care additive solution of the present invention are used to clean the skin or remove makeup or used in other activities, they can not only have antibacterial and disinfection effects, but also have good moisturizing effect for the skin, and further have a certain degree of whitening, repairing and calming effects.

In addition, the base material of the antibacterial skin care wet wipe of the present invention adopts a wood pulp spunlaced non-woven fabric or a cotton spunlaced non-woven fabric. These two non-woven fabrics are all natural fiber components, which have better water absorption properties, and have more softer hand-feeling than ordinary non-woven fabrics, thereby the wet wipes of the invention have no irritation to skin and are suitable for sensitive skin.

DETAILED DESCRIPTION OF THE INVENTION

The present invention is further described in combination with the embodiments. Those skilled in the art may understand the following embodiments are only used to explain the present invention and not intended to limit the scope of the present invention.

Example 1

An antibacterial wet wipe for skin care, which is prepared by adding an antibacterial skin care additive solution to a spunlaced non-woven fabric which is used as a base material. First, preparing the antibacterial skin care additive solution, weighing the following components according to the formula of the antibacterial skin care additive solution of the invention:

Tea tree essential oil 5%,
Nano silver 2%,
Neroli essential oil 4%,
Ceramide 1%,
Glycerin 1%,
Carbomer 0.1%,
Deionized water balance, The nano silver is derived from a nano silver solution with a concentration of 800 ppm and an average particle size of 5 nm. Adding the weighed components to a stirred tank to uniformly mix all the components, then sterilizing the mixed solution by $Co^{60}$-$\gamma$ ray, thereby obtaining example A of the antibacterial skin care additive solution of the invention;

Second, sterilizing the spunlace nonwoven fabric by the dry heat sterilization method, then flattening the spunlace nonwoven fabric in a container, adding sufficient amount of antibacterial skin care additive solution into the container and standing still for a certain period of time until the spunlaced nonwoven fabric is completely infiltrated, thereby obtaining the antibacterial wipe sample A of the present invention.

Example 2

An antibacterial wet wipe for skin care, which is prepared by adding an antibacterial skin care additive solution to a wood pulp spunlaced non-woven fabric which is used as a base material.

First, preparing the antibacterial skin care additive solution, weighing the following components according to the formula of the antibacterial skin care additive solution of the invention:

Tea tree essential oil 10%,
Nano silver 4%,
Neroli essential oil 5%,
Ceramide 1.5%,
Glycerin 2%,
Water-soluble vitamin E 2%,
Carbomer 0.5%,
Deionized water balance, the nano silver is derived from a nano silver solution with a concentration of 1000 ppm and an average particle size of 3 nm. Adding the weighed components to a stirred tank to uniformly mix all the components, then sterilizing the mixed solution by ultraviolet sterilization method, thereby obtaining example B of the antibacterial skin care additive solution of the invention;

Second, sterilizing the wood pulp spunlace nonwoven fabric by the $Co^{60}$-γ ray, then flattening the wood pulp spunlace nonwoven fabric in a container, adding sufficient amount of antibacterial skin care additive solution into the container and standing still for a certain period of time until the wood pulp spunlaced nonwoven fabric is completely infiltrated, thereby obtaining the antibacterial wipe sample B of the present invention.

Example 3

An antibacterial wet wipe for skin care, which is prepared by adding an antibacterial skin care additive solution to a cotton spunlaced non-woven fabric which is used as a base material.

First, preparing the antibacterial skin care additive solution, weighing the following components according to the formula of the antibacterial skin care additive solution of the invention:

Medical tea tree essential oil 8%,
Nano silver 3%,
Neroli essential oil 3%,
Ceramide 1.2%,
Glycerin 3%,
Water-soluble vitamin E 2%,
Carbomer 0.3%,
Deionized water balance, the nano silver is derived from a nano silver solution with a concentration of 500 ppm and an average particle size of 4 nm. Adding the weighed components to a stirred tank to uniformly mix all the components, then sterilizing the mixed solution by microwave sterilization method, thereby obtaining example C of the antibacterial skin care additive solution of the invention;

Second, sterilizing the cotton spunlace nonwoven fabric by the moist heat sterilization method, then flattening the cotton spunlace nonwoven fabric in a container, adding sufficient amount of antibacterial skin care additive solution into the container and standing still for a certain period of time until the cotton spunlaced nonwoven fabric is completely infiltrated, thereby obtaining the antibacterial wipe sample C of the present invention.

Example 4

An antibacterial wet wipe for skin care, which is prepared by adding an antibacterial skin care additive solution to a cotton spunlaced non-woven fabric which is used as a base material.

First, preparing the antibacterial skin care additive solution, weighing the following components according to the formula of the antibacterial skin care additive solution of the invention:

Medical tea tree essential oil 6%,
Nano silver 4%,
Neroli essential oil 5%,
Ceramide 1.3%,
Glycerin 3%,
Water-soluble vitamin E 3%,
Carbomer 0.2%,
Deionized water balance, the nano silver is derived from a nano silver solution with a concentration of 600 ppm and an average particle size of 2 nm. Adding the weighed components to a stirred tank to uniformly mix all the components, then sterilizing the mixed solution by $Co^{60}$-γ ray, thereby obtaining example D of the antibacterial skin care additive solution of the invention;

Second, sterilizing the cotton spunlace nonwoven fabric by the moist heat sterilization method, then flattening the cotton spunlace nonwoven fabric in a container, adding sufficient amount of antibacterial skin care additive solution into the container and standing still for a certain period of time until the cotton spunlaced nonwoven fabric is completely infiltrated, thereby obtaining the antibacterial wipe sample D of the present invention.

Antibacterial Effect Tests

According to GB15979-2002, the antibacterial wet wipes for skin care samples A-D prepared in Examples 1-4 were tested under the defined test conditions and the results are listed in Table 2:

TABLE 2

| | | Antibacterial effect tests | | | |
| --- | --- | --- | --- | --- | --- |
| | Tested | Sterilization rate % | | | |
| Tested bacteria | time | A | B | C | D |
| Staphylococcus | 2 min | 99.50 | 100 | 99.85 | 99.98 |
| aureus | 5 min | 100 | 100 | 100 | 100 |
| Escherichia | 2 min | 99.60 | 100 | 99.90 | 99.95 |
| coli | 5 min | 100 | 100 | 100 | 100 |
| Candida | 2 min | 99.32 | 99.90 | 99.93 | 99.73 |
| albicans | 5 min | 100 | 100 | 100 | 100 |

According to the above contents and data, it can be seen that the antibacterial wet wipes of the present invention have excellent cleaning and bactericidal effects, and the sterilization rate of *Staphylococcus aureus, Escherichia coli*, and *Candida albicans* can reach 100% in 5 minutes. Since the tea tree essential oil and neroli essential oil added in the antibacterial wet wipes are plant extracts, and the nano silver has no irratation and is safe to human body, the ceramide itself is a component of the body skin, so the antibacterial wet wipes of the invention can also be used to clean the skin on hands, arms, feet, etc. It can also be used to clean the skin of other parts of the body, such as the skin on face and perineum where the skin is much more sensitive and vulnerable. Due to the added neroli essential oil, ceramide, glycerin and water-soluble vitamin E, it will have a good skin feeling after using the wet wipes, and there is no feeling of air drying and tightness, and even subsequent moisturizing skin care products does not need to be applied. Otherwise, long-term use will not cause harm to the skin, and in contrast the neroli essential oil and ceramide and other components will have a certain degree of skin whitening and repairing effects.

The above description is merely preferred embodiments of the present invention, and it is not intended to limit the present invention in any forms. Those skilled in the art can modify or improve the contents of the present invention. Therefore, any simple modification, equivalent replacement and the like made by those skilled in the art according to the spirits and essential contents of the present invention will fall within the protection scope of the present invention without departing from the technical solutions of the present invention.

That which is claimed:

1. An antibacterial wet wipe for skin care, wherein the wipe is prepared by adding an antibacterial skin care additive solution to a spunlaced non-woven fabric which is used as a base material, wherein the antibacterial skin care additive solution consists of the following components by mass fraction:

Tea tree essential oil 5-10%,
   Nano silver 2-4%,
   Neroli essential oil 3-5%,
   Ceramide 1-1.5%,
   Glycerin 1-3%,
   Water-soluble vitamin E 0-3%,
   Emulsifier 0.1-0.5%, and
   Deionized water balance,
   wherein the nano silver is derived from a nano silver solution with a mass percentage concentration from 500 ppm to 1000 ppm and the average particle size of the nano silver is 1-5 nm, and
   wherein the emulsifier is carbomer.

2. The antibacterial wet wipe for skin care according to claim 1, wherein the tea tree essential oil is medical tea tree essential oil.

3. The antibacterial wet wipe for skin care according to claim 1, wherein the tea tree essential oil has a mass fraction of 6-8% in the antibacterial skin care additive solution.

4. The antibacterial wet wipe for skin care according to claim 1, wherein the spunlaced non-woven fabric is a wood pulp spunlaced non-woven fabric or a cotton spunlaced non-woven fabric.

5. A method for preparing the antibacterial wet wipe for skin care of claim 1, comprising sterilizing the spunlace nonwoven fabric, then flattening the spunlace nonwoven fabric in a container, adding a sufficient amount of antibacterial skin care additive solution into the container and standing still for a certain period of time until the spunlaced nonwoven fabric is completely infiltrated.

6. The method for preparing the antibacterial wet wipe for skin care according to claim 5, wherein the sterilizing method is a radiation sterilization method, wet heat sterilization method or dry heat sterilization method.

7. The method for preparing the antibacterial wet wipe for skin care according to claim 6, wherein the radiation sterilization method is $Co^6$-γ ray, ultraviolet or microwave sterilization method.

* * * * *

UNITED STATES PATENT AND TRADEMARK OFFICE
CERTIFICATE OF CORRECTION

PATENT NO. : 10,456,437 B1
APPLICATION NO. : 15/986115
DATED : October 29, 2019
INVENTOR(S) : Shulan Jiang Page 1 of 1

It is certified that error appears in the above-identified patent and that said Letters Patent is hereby corrected as shown below:

On the Title Page

Item (71) Applicant: Please correct "Jiangmen" to read -- Jiangmen City --

Item (72) Inventor: Please correct "Jiangmen" to read -- Jiangmen City --

In the Claims

Column 8, Line 27, Claim 7: Please correct "$Co^6$-γ" to read -- $Co^{60}$-γ --

Signed and Sealed this
Twenty-fifth Day of February, 2020

Andrei Iancu
*Director of the United States Patent and Trademark Office*